United States Patent
Asahi et al.

(10) Patent No.: US 10,844,444 B2
(45) Date of Patent: Nov. 24, 2020

(54) METHOD OF PRODUCING SUGAR SOLUTION

(71) Applicant: Toray Industries, Inc., Tokyo (JP)

(72) Inventors: Yuka Asahi, Kamakura (JP); Atsushi Minamino, Kamakura (JP); Hiroyuki Kurihara, Kamakura (JP); Masashi Higasa, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/557,606

(22) PCT Filed: Mar. 23, 2016

(86) PCT No.: PCT/JP2016/059079
§ 371 (c)(1),
(2) Date: Sep. 12, 2017

(87) PCT Pub. No.: WO2016/152883
PCT Pub. Date: Sep. 29, 2016

(65) Prior Publication Data
US 2018/0051350 A1    Feb. 22, 2018

(30) Foreign Application Priority Data
Mar. 24, 2015    (JP) ................. 2015-061103

(51) Int. Cl.
*C13K 1/02*    (2006.01)
*B01D 65/02*    (2006.01)
(Continued)

(52) U.S. Cl.
CPC ............. *C13K 1/02* (2013.01); *B01D 61/14* (2013.01); *B01D 61/147* (2013.01); *B01D 61/16* (2013.01);
(Continued)

(58) Field of Classification Search
CPC ....................................................... C13K 1/02
(Continued)

(56) References Cited

U.S. PATENT DOCUMENTS

| 5,410,021 A | * | 4/1995 | Kampen | ................. A23J 1/12 127/67 |
| 5,932,452 A | * | 8/1999 | Mustranta | ............. C12N 11/02 435/105 |

(Continued)

FOREIGN PATENT DOCUMENTS

| EP | 2650384 A1 | 10/2013 |
| JP | 61-234790 A | 10/1986 |

(Continued)

OTHER PUBLICATIONS

Effect of Xylan and Lignin Removal by Batch and Flowthrough Pretreatment on the Enzymatic Digestibility of Corn Stover Cellulose Bin Yang, Charles E. Wyman Biotechnology and Bioengineering, vol. 86, No. 1 pp. 88-95 (Year: 2004).*

(Continued)

*Primary Examiner* — Douglas B Call
(74) *Attorney, Agent, or Firm* — DLA Piper LLP (US)

(57) ABSTRACT

A method of producing a sugar liquid derived from a cellulose-containing biomass includes (a) saccharifying a pretreated product having alignin content of not more than 8.5% obtained by pretreatment of a cellulose-containing biomass, to obtain a saccharified liquid; (b) filtering the saccharified liquid obtained in Step (a) through a microfiltration membrane to allow formation of a cake on a membrane surface in a feed side while obtaining a sugar liquid from a permeate side; and (c) collecting the cake formed on the membrane surface in Step (b) by peeling from the membrane.

15 Claims, 1 Drawing Sheet

(51) Int. Cl.
  *C12P 19/14* (2006.01)
  *B01D 61/14* (2006.01)
  *B09B 3/00* (2006.01)
  *B01D 61/16* (2006.01)
  *C13B 20/16* (2011.01)

(52) U.S. Cl.
  CPC ............. *B01D 65/02* (2013.01); *B09B 3/00* (2013.01); *C12P 19/14* (2013.01); *C13B 20/165* (2013.01); *B01D 2311/04* (2013.01); *B01D 2311/06* (2013.01); *B01D 2311/263* (2013.01); *B01D 2311/2676* (2013.01); *B01D 2311/2688* (2013.01); *B01D 2315/10* (2013.01); *B01D 2321/04* (2013.01); *B01D 2321/185* (2013.01)

(58) Field of Classification Search
  USPC ......................................................... 127/37
  See application file for complete search history.

(56) References Cited

U.S. PATENT DOCUMENTS

| | | | | |
|---|---|---|---|---|
| 2009/0120873 | A1* | 5/2009 | Becker | B01D 65/00 210/636 |
| 2010/0263814 | A1* | 10/2010 | Dottori | D21B 1/36 162/21 |
| 2011/0250637 | A1* | 10/2011 | Kurihara | C13K 13/002 435/41 |
| 2013/0004994 | A1 | 1/2013 | Hanakawa | |
| 2013/0092157 | A1* | 4/2013 | Hanakawa | C13B 20/165 127/53 |
| 2013/0266991 | A1* | 10/2013 | Kanamori | B01D 61/16 435/99 |
| 2014/0061126 | A1* | 3/2014 | Dominiak | C02F 3/006 210/609 |
| 2014/0106418 | A1* | 4/2014 | Parekh | C12P 7/20 435/134 |

FOREIGN PATENT DOCUMENTS

| | | |
|---|---|---|
| JP | 09-507386 A | 7/1997 |
| JP | 2011-223975 A | 11/2011 |
| JP | 2012-527886 A | 11/2012 |
| JP | 2013-143932 A | 7/2013 |
| JP | 2015-029463 A | 2/2015 |
| WO | 2010/067785 A1 | 6/2010 |
| WO | WO2011/162009 * | 12/2011 |
| WO | WO2012077697 * | 6/2012 |
| WO | 2014/136711 A1 | 9/2014 |

OTHER PUBLICATIONS

Extended European Search Report dated Nov. 8, 2018, of counterpart European Patent Application No. 16768786.2.

* cited by examiner

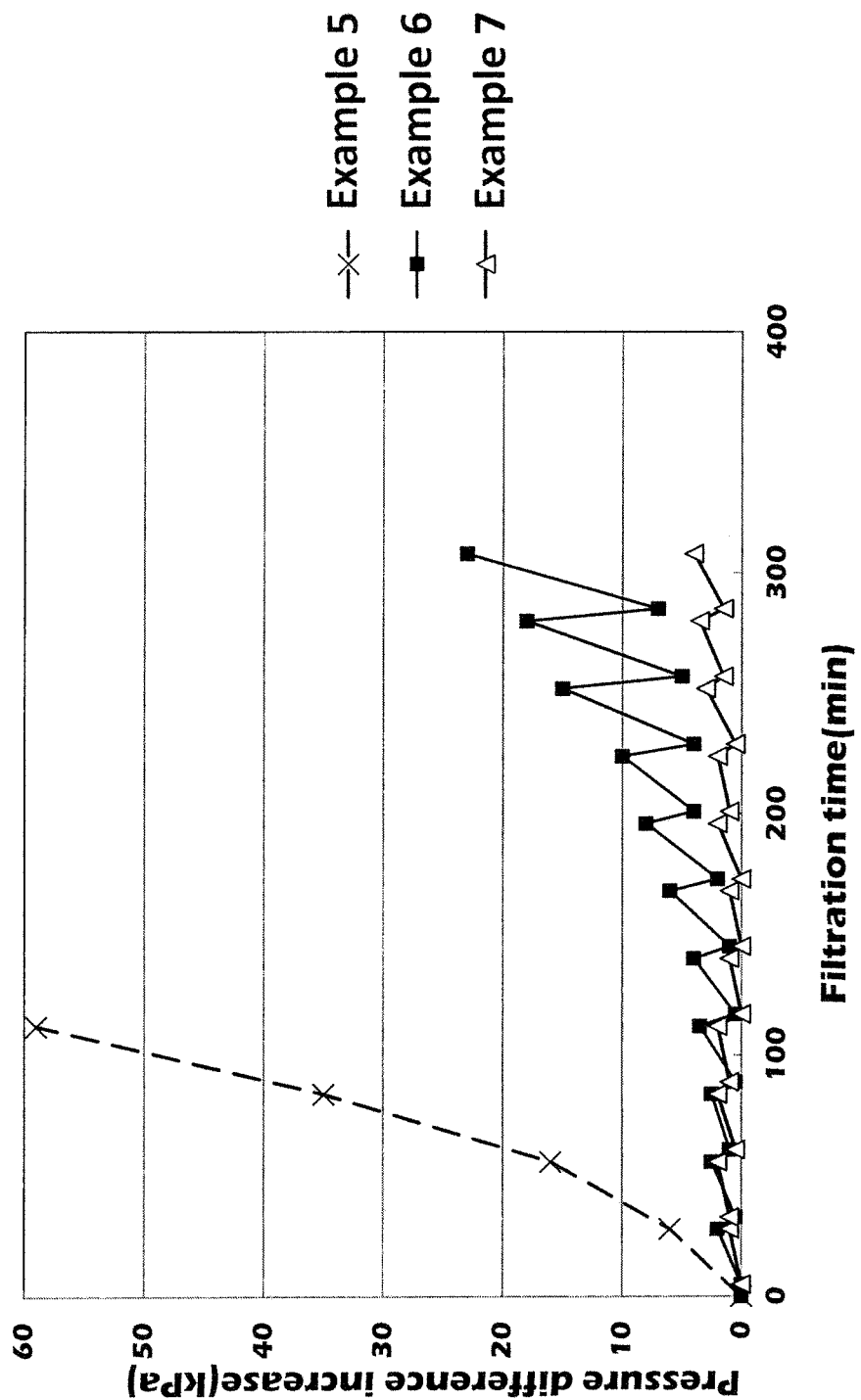

METHOD OF PRODUCING SUGAR SOLUTION

TECHNICAL FIELD

This disclosure relates to a method of producing a sugar liquid from a cellulose-containing biomass.

BACKGROUND

In recent years, because of problems such as global warming and depletion of petroleum resources, and from the viewpoint of carbon neutrality, use of biomass as an alternative to petroleum products has been attracting attention. In particular, production of ethanol and chemical products from non-edible cellulose-containing biomass, which does not compete with food, has been expected.

Production of ethanol or a chemical product from a cellulose-containing biomass requires the following series of processes. First, the cellulose-containing biomass is pretreated to perform saccharification of cellulose and hemicellulose, which are polysaccharides. Subsequently, the solid component other than fermentable sugars, and fermentation-inhibiting substances, contained in the saccharified liquid are removed. The resulting product is then concentrated and purified to achieve a sugar concentration suitable for fermentation. As methods of removing the solid component from a saccharified liquid obtained in a saccharification process, methods using a screw press or filter press (Japanese Translated PCT Patent Application Laid-open No. 9-507386 and JP 2013-143932 A), a method using centrifugation (JP 61-234790 A) and the like have been studied so far.

However, those methods require large-scale solid-liquid separation devices, and are costly from the viewpoint of the equipment cost and the operation cost, which has been problematic. Moreover, some membrane clogging components derived from cellulose-containing biomass cannot be completely removed by those solid-liquid separation devices, and insufficient removal of the solid component places a burden on a later process of purification and concentration. In view of this, a technique in which treatment in a large-scale solid-liquid separation device is followed by treatment with a microfiltration membrane (JP 2011-223975 A) has been proposed. However, this led to a further increase in the cost for the process of sugar liquid purification.

In a process of producing a sugar liquid derived from a cellulose-containing biomass, a saccharified liquid obtained by saccharification of a pretreated product of the biomass has been conventionally subjected to solid-liquid separation using a filter press, screw press, centrifugation and/or the like. However, there have been problems such as an increase in the size of the equipment, high operation cost and the like. Further, we found another problem that a saccharified liquid obtained by saccharification of a pretreated product of cellulose-containing biomass having a lignin content of not more than 8.5% may show insufficient separation in a conventional solid-liquid separation method such as use of a filter press, screw press and/or centrifugation. It could therefore be helpful to achieve significant reduction of the cost of a sugar liquid production process, by saccharifying a pretreated product of biomass having a lignin content of not more than 8.5% and directly filtering the resulting saccharified liquid through a microfiltration membrane, thereby avoiding use of a large-scale solid-liquid separation device.

SUMMARY

We discovered that a sugar liquid can be obtained by microfiltration membrane treatment of a saccharified liquid of a pretreated product of cellulose-containing biomass having a lignin content of not more than 8.5%, and that, by peeling-off and collection of a cake formed on the membrane surface of the microfiltration membrane, solid-liquid separation with the microfiltration membrane can be carried out while suppressing clogging of the membrane.

We thus provide (1) to (10) below:

(1) A method of producing a sugar liquid derived from a cellulose-containing biomass, the method comprising the steps of:
  (a) saccharifying a pretreated product having a lignin content of not more than 8.5% obtained by pretreatment of a cellulose-containing biomass, to obtain a saccharified liquid;
  (b) filtering the saccharified liquid obtained in Step (a) through a microfiltration membrane to allow formation of a cake on the membrane surface in the feed side while obtaining a sugar liquid from the permeate side; and
  (c) collecting the cake formed on the membrane surface in Step (b) by peeling off from the membrane.

(2) The method of producing a sugar liquid according to (1), wherein the pretreated product of a cellulose-containing biomass is a chemical pulp.

(3) The method of producing a sugar liquid according to (1) or (2), wherein the lignin content in the pretreated product of a cellulose-containing biomass is not more than 6%.

(4) The method of producing a sugar liquid according to any one of (1) to (3), wherein the filtration method in Step (b) is cross-flow filtration.

(5) The method of producing a sugar liquid according to (4), wherein the membrane surface linear velocity in the cross-flow filtration is from 10 cm/sec. to 30 cm/sec.

(6) The method of producing a sugar liquid according to any one of (1) to (5), wherein the collection method in Step (c) is collection of the cake formed on the membrane surface by backwashing and/or air washing.

(7) The method of producing a sugar liquid according to (6), wherein an aqueous solution at a pH of not less than 6 is used for the backwashing.

(8) The method of producing a sugar liquid according to any one of (1) to (7), further comprising Step (d) of performing solid-liquid separation of the collected product obtained in Step (c) and collecting a liquid fraction.

(9) The method of producing a sugar liquid according to (8), wherein, in Step (d), the pH of the collected product obtained in Step (c) is adjusted to not less than 6 followed by performing the solid-liquid separation.

(10) The method of producing a sugar liquid according to (8) or (9), wherein the liquid fraction obtained in Step (d) is subjected to Step (a).

A saccharified liquid obtained by saccharification of a pretreated product of cellulose-containing biomass having a lignin content of not more than 8.5% is filtered through a microfiltration membrane to obtain a sugar liquid in the permeate side while efficiently allowing formation of a cake on the membrane surface of the feed side and collecting the cake by peeling off from the membrane. By this, the solid component in the enzymatically saccharified liquid of the cellulose-containing biomass can be separated, and a sugar liquid can be obtained at low cost without use of a large-scale solid-liquid separation device that requires high equipment cost.

BRIEF DESCRIPTION OF THE DRAWINGS

FIG. 1 is a graph showing differences in the trend of increase in the pressure difference among solid-component peeling methods.

DETAILED DESCRIPTION

A cellulose-containing biomass is a biomass containing cellulose, which is a polymer containing glucose linked through β-1,4 bonds. Examples of a cellulose-containing biomass include herbaceous biomasses such as bagasse, switchgrass, napier grass, *Erianthus*, corncob, corn stover, rice straw, and wheat straw; and woody biomasses such as waste wood, pulp, waste paper, and wood. In general, such cellulose-containing biomasses contain hemicellulose, which is a polysaccharide, and lignin, which is a phenylpropanoid polymer, as major components besides cellulose.

In a cellulose-containing biomass, lignin is distributed in a manner in which polysaccharides are covered therewith. Thus, lignin prevents enzymes from acting on the polysaccharides. Therefore, in general, a cellulose-containing biomass is subjected to a mechanical and/or chemical pretreatment before its saccharification to perform partial degradation or removal of lignin. In Step (a), a saccharified liquid is obtained from a pretreated product of cellulose-containing biomass having a lignin content of not more than 8.5% prepared by such a pretreatment.

The pretreated product of cellulose-containing biomass having a lignin content of not more than 8.5% may also be a product obtained by removing lignin by pretreatment to decrease the lignin content to not more than 8.5%. The method of the pretreatment is not limited, and examples of the method include methods in which a lignin-degrading white-rot fungus or an enzyme produced by a white-rot fungus is used, and chemical pulping. A chemical pulp prepared by removal of lignin by chemical pulping is more preferred. The lignin content is not limited as long as it is not more than 8.5%. The lignin content is preferably not more than 6%, more preferably not more than 4%. The lignin content is preferably not less than 0.2%, more preferably not less than 0.5%. The lignin content is preferably from 0.2% to 8.5%, more preferably from 0.5% to 8.5%, still more preferably from 0.2% to 6.0%, especially preferably from 0.5% to 6.0%.

The chemical pulping means removal of lignin from a cellulose-containing biomass by chemical treatment. Specific examples of the chemical pulping include, but are not limited to, kraft pulping, sulfite pulping, organosolv pulping, and soda pulping. Pulping that is generally called semi-chemical pulping, which is a combination of such chemical pulping and mechanical pulping, is not distinguished from the chemical pulping as long as chemical treatment is carried out.

In kraft pulping, a pulp is obtained by cooking with a mixture of NaOH and $Na_2S$.

In sulfite pulping, a pulp is obtained by digestion using a sulfite. The digestion is carried out under various pH conditions such as alkaline, neutral, or acidic conditions.

Organosolv pulping is digestion using an organic solvent. Specific examples of the organic solvent include, but are not limited to, acetic acid and alcohols.

Soda pulping is digestion using a sodium hydroxide solution.

Among these pulping treatments, kraft pulping is more preferred because of the amount of production.

The cellulose-containing biomass to be subjected to the pulping treatment is not limited. From the viewpoint of supply, woody biomasses are preferred since they are now used for industrial production of a large amount of chemical pulps.

Pulps produced in the paper industry may also be used. Examples of such pulps include bleached pulps and unbleached pulps. From the viewpoint of the cost, unbleached pulps are preferred.

In chemical pulp, lignin has been removed by chemical pulping. Since a part of hemicellulose is also degraded in this process, the ratio of cellulose in the constituting components of chemical pulp is high. Cellulose is a glucan in which glucose is linked through β-1,4 bonds. A chemical pulp therefore has a high glucan content. The ratio of glucan with respect to the dry weight of the chemical pulp is preferably not less than 65%, more preferably not less than 70%. The glucan content can be determined by measurement of the amount of cellulose. However, the glucan content (%) is simply calculated based on the amount of glucose obtained by forced degradation of the pretreated product of cellulose-containing biomass into monosaccharides by acid hydrolysis.

The lignin content is the content of lignin with respect to the dry weight of the pretreated product of cellulose-containing biomass, and can be calculated according to Equation (1):

$$\text{Lignin content (\%)} = \text{amount of lignin in the pretreated product of cellulose-containing biomass (g)/dry weight of the pretreated product of cellulose-containing biomass (g)} \times 100 \quad (1).$$

The amount of lignin in the pretreated product of cellulose-containing biomass means the content of acid-insoluble lignin. Acid-insoluble lignin is also called Klason lignin, and it is prepared by adding 72% (w/w) sulfuric acid to a cellulose-containing biomass to cause swelling and partial hydrolysis of polysaccharides, adding water to the resulting product to dilute the sulfuric acid, performing autoclaving to cause hydrolysis of the polysaccharides to make them acid-soluble, and then removing the ash component from the resulting insoluble fraction. Measurement of the amount of acid-insoluble lignin can be carried out by referring to A. Sluiter and seven other authors, "Determination of Structural Carbohydrates and Lignin in Biomass," National Renewable Energy Laboratory (NREL), April 2008, Revision August 2012. Specifically, the measurement can be carried out by adding 3 mL of 72% (w/w) sulfuric acid to 0.3 g of a cellulose-containing biomass, leaving the resulting mixture to stand at 30° C. for 1 hour (while stirring the mixture several times), adding 84 mL of purified water to the mixture to a sulfuric acid concentration of 4%, and then performing autoclaving at 120° C. for 1 hour to hydrolyze polysaccharides.

By measuring the monosaccharide concentration in the hydrolysate after the hydrolysis to calculate the amount of monosaccharides produced by the hydrolysis, the glucan content (%) with respect to the dry weight of the pretreated product of cellulose-containing biomass can be calculated according to Equation (2). The condensation coefficient of glucan is 0.90.

Glucan content (%)=condensation coefficient×
amount of glucose produced (g)/dry weight of
the pretreated product of cellulose-containing
biomass (g)×100     (2)

The saccharified liquid obtained in Step (a) means a liquid prepared by saccharifying cellulose and hemicellulose, which are polysaccharides, in the pretreated product of cellulose-containing biomass to perform hydrolysis into monosaccharides and oligosaccharides. Examples of the method of the saccharification include acid saccharification using sulfuric acid or the like, and hydrolysis by enzymatic saccharification using a saccharifying enzyme. Enzymatic saccharification using a saccharifying enzyme is preferred.

The enzymatic saccharification is a method in which a pretreated product of cellulose-containing biomass is reacted with a saccharifying enzyme having an activity to degrade cellulose or hemicellulose, or with a saccharifying enzyme that aids degradation of cellulose or hemicellulose, to allow saccharification. Specific examples of the enzyme component include cellobiohydrolase, endoglucanase, exo-glucanase, β-glucosidase, xylanase, and xylosidase, and biomass-swelling enzymes. The saccharifying enzyme is preferably an enzyme mixture containing a plurality of types of these components. Since hydrolysis of, for example, cellulose and hemicellulose can be efficiently carried out by a coordinate effect or complementary effect by such a plurality of enzyme components, such an enzyme mixture is preferably used.

A saccharifying enzyme produced by a microorganism may be preferably used. For example, the saccharifying enzyme may contain a plurality of enzyme components produced by a single type of microorganism, or may be a mixture of enzyme components produced by a plurality of types of microorganisms.

The microorganism that produces a saccharifying enzyme is a microorganism that intracellularly or extracellularly produces a saccharifying enzyme, preferably a microorganism that extracellularly produces a saccharifying enzyme. This is because the saccharifying enzyme can be more easily recovered from the microorganism if the microorganism extracellularly produces the saccharifying enzyme.

The microorganism that produces a saccharifying enzyme is not limited as long as the microorganism produces the above-described enzyme component(s). A filamentous fungus classified as *Trichoderma* can be especially preferably used as the microorganism that produces a saccharifying enzyme since it extracellularly secretes a large amount of various saccharifying enzymes.

The saccharifying enzyme is preferably a saccharifying enzyme derived from a *Trichoderma* fungus. More specifically, the saccharifying enzyme is more preferably derived from *Trichoderma reesei*. Still more specifically, the saccharifying enzyme is preferably derived from a *Trichoderma* fungus such as *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, or *Trichoderma viride* QM9123 (*Trichoderma viride* 9123). The saccharifying enzyme may also be derived from a mutant strain prepared from a *Trichoderma* filamentous fungus by mutagenesis using a mutagen, UV irradiation, or the like to enhance the productivity of the saccharifying enzyme. For example, the saccharifying enzyme may be a saccharifying enzyme having a modified composition ratio derived from a mutant strain that was prepared by altering a *Trichoderma* filamentous fungus such that expression of a part of the enzyme components is enhanced.

A commercially available saccharifying enzyme derived from a *Trichoderma* fungus may also be used. Examples of such a saccharifying enzyme include "Cellic CTec (registered trademark)," manufactured by Novozymes Japan; "Accellerase 1000 (registered trademark)" and "Accellerase 1500 (registered trademark)," manufactured by Genencor Kyowa; and "Cellulase from *Trichoderma reesei* ATCC 26921," "Cellulase from *Trichoderma viride*" and "Cellulase from *Trichoderma longibrachiatum*," manufactured by Sigma Aldrich Japan.

The hydrolysis reaction using a saccharifying enzyme is carried out preferably at a pH of about 3 to 7, more preferably at a pH of 4.0 to 6.0. The reaction temperature is preferably 40 to 70° C. The pH can be adjusted by adding an acid and/or an alkali as appropriate, or by adding a pH buffering agent such as an acetic acid salt or a citric acid salt. From an economic point of view, and from the viewpoint of fermentation inhibition, a method using an aqueous solution of sulfuric acid as the acid, and an aqueous solution of sodium hydroxide, calcium hydroxide, or ammonia as the alkali, wherein the acid and/or alkali is/are added over time while measuring the pH during the reaction such that a desired pH is achieved, is preferred. The length of time of the hydrolysis reaction by the saccharifying enzyme is preferably from 1 hour to 72 hours from the viewpoint of the yield, more preferably from 3 hours to 24 hours from the viewpoint of the energy used. The reaction apparatus to be used in the hydrolysis may be either a single-stage apparatus or a multi-stage apparatus, or may be a continuous type apparatus.

The initial solid component concentration (w/w) upon the preparation of the saccharified liquid of the pretreated product of cellulose-containing biomass is not limited, and is preferably a concentration at which stirring is possible so that hydrolase can be allowed to react sufficiently. Since mixing of a chemical pulp is especially difficult, the initial solid component concentration (w/w) is preferably 5 to 10% for allowing sufficient stirring.

Subsequently, the saccharified liquid obtained in Step (a) is subjected to Step (b) of filtering the saccharified liquid through a microfiltration membrane to allow formation of a cake on the membrane surface in the feed side while obtaining a sugar liquid from the permeate side.

The microfiltration membrane used in Step (b) is a membrane having an average pore size of 0.01 μm to 5 mm, which is called microfiltration, MF membrane, or the like for short. To concentrate the solid component on the membrane surface, and prevent clogging in the inside of the membrane, the average pore size is preferably not more than 0.45 μm, more preferably not more than 0.22 μm.

Examples of the material of the microfiltration membrane include celluloses, aromatic polyamide, polyvinyl alcohol, polysulfone, polyvinylidene fluoride, polyethylene, polyacrylonitrile, polypropylene, polycarbonate, polytetrafluoroethylene, ceramics, and metals. Preferred among these are aromatic polyamide, polyvinyl alcohol, polysulfone, polyvinylidene fluoride, polyethylene, polyacrylonitrile, polypropylene, polycarbonate, and polytetrafluoroethylene since these are not influenced by saccharifying enzymes contained in the enzymatically saccharified liquid, and have excellent ability to remove the insoluble solid component. Polyvinylidene fluoride is especially preferred.

Examples of the shape of the membrane include hollow fiber membranes, tubular membranes, and flat membranes.

In cases where backwashing is carried out, a hollow fiber membrane or a tubular membrane is preferred.

The permeation flux during the filtration through the microfiltration membrane is preferably not more than 2.0 m/day, more preferably not more than 1.0 m/day from the viewpoint of preventing clogging of the membrane. The permeation flux herein means the permeation flow rate per unit time per unit membrane area, and can be calculated according to Equation (3):

$$\text{Permeation flux (m/day)} = \text{permeate volume (m}^3\text{)}/\text{membrane area (m}^2\text{)/filtration time (day)} \quad (3).$$

The clogging of the membrane can be evaluated by an increase in the transmembrane pressure difference or a decrease in the filtration flow volume. The transmembrane pressure difference means the difference in the pressure between the feed side and the permeate side of the membrane, and can be calculated according to Equation (4) by measurement of the module-inlet pressure ($P1$), module-outlet pressure ($P2$), and permeate-side pressure ($P3$):

$$\text{Transmembrane pressure difference} = (P1+P2)/2 - P3 \quad (4).$$

In constant flow filtration, in which the permeation flux is kept constant, the transmembrane pressure difference increases as clogging of the membrane proceeds. On the other hand, in constant pressure filtration, in which the transmembrane pressure difference is kept constant, the permeation flow rate decreases as clogging of the membrane proceeds. To prevent a decrease in the filtration performance, the transmembrane pressure difference is not more than 50 kPa, preferably not more than 20 kPa.

The filtration method is not limited, and preferably cross-flow filtration. The membrane surface linear velocity in the cross-flow filtration is preferably from 10 to 50 cm/sec., more preferably from 10 to 30 cm/sec.

Formation of a cake on the membrane surface in Step (b) means formation of a cake layer by attachment of the solid component on the membrane surface. From the viewpoint of efficiently allowing formation of a cake on the membrane surface in Step (b), the saccharified liquid obtained in Step (a) is preferably directly filtered through the microfiltration membrane.

Formation of a cake in Step (b) can be evaluated as a decrease in the solid component ratio in the saccharified liquid observed after filtration of a predetermined volume of saccharified liquid by total circulation operation for a predetermined length of time. The total circulation operation is an operation method in which the filtrate in the permeate side is returned to the feed side, and formation of a cake on the membrane surface occurs over the operation time. The amount of the cake formed on the membrane surface can be evaluated based on the solid component ratio (%), which is the ratio of the solid component concentration in the saccharified liquid after the total circulation operation to the solid component concentration in the saccharified liquid before the start of the filtration, which is taken as 100%. Since the solid component forming the cake is separated from the saccharified liquid, the solid component ratio (%) in the saccharified liquid decreases as the formation of the cake proceeds. The solid component ratio (%) is calculated according to Equation (5):

$$\text{Solid component ratio (\%)} = \text{solid component concentration in the saccharified liquid/solid component concentration in the saccharified liquid after the total circulation filtration operation} \times 100 \quad (5).$$

As the solid component concentration, the MLSS concentration (Mixed Liquor Suspended Solids) may be used. Measurement of MLSS can be carried out according to JIS K 0102 14.1 (2008), which is based on the Japanese Industrial Standard.

In batch operation, the amount of the solid component in the feed side of the microfiltration membrane decreases due to formation of a cake and discharging of the cake.

In continuous operation, the amount of the solid component in the feed side of the microfiltration membrane can be kept constant by setting operation conditions such that the amount of the solid component separated is the same as the amount of the solid component supplied.

Subsequently, in Step (c), the cake formed on the membrane surface in Step (b) is peeled off and collected.

Examples of the method for peeling off the cake formed on the membrane surface include a method in which water or a reagent solution is allowed to pass through only the feed side of the membrane, a method in which the membrane is immersed in water or a reagent solution, and a method in which backwashing, air washing, and/or a sponge ball is/are used. A method in which backwashing and air washing are used in combination is effective and preferred. Before carrying out the peeling-off operation, the solution in the feed side of the microfiltration membrane module is preferably removed to the outside of the module. The method for the removal of the solution to the outside of the module is preferably a method in which the solution is removed from the bottom part of the module. The solution removed to the outside of the module may be discharged to the outside of the filtration process, or may be collected together with the cake that is peeled off.

The backwashing means passing of a washing liquid for peeling-off of the cake from the permeate side to the feed side of the membrane. Examples of the washing liquid include the filtrate of the microfiltration membrane, water, and reagent solutions. In particular, when the washing liquid is collected to the outside of the filtration system, water or a reagent solution is preferred from the viewpoint of prevention of loss of the filtrate, which is the product of interest. The pH of the washing liquid is not limited, and may be adjusted preferably to not less than 5, more preferably to not less than 6. The flow rate during the backwashing may vary depending on the saccharified liquid to be filtered. It is preferably about one to three times larger than the permeation flow rate. The frequency and the length of time of the backwashing may also vary depending on the saccharified liquid. For example, the backwashing may be carried out periodically at intervals of 10 to 180 minutes, and the length of time of each backwashing operation may be 10 seconds to 10 minutes. The backwashing liquid containing the peeled cake is preferably collected from the bottom part of the module, similarly to the solution in the feed side in the module.

The air washing is a method in which a gas is supplied to the feed side of the membrane to peel off the cake formed on the membrane surface.

By the peeling-off and collection of the cake formed on the membrane surface, clogging of the membrane surface can be prevented. Therefore, by repeating Step (a) and Step (b), filtration can be continued without causing a decrease in the filtration performance.

The collected product obtained in Step (c) may be simply discarded, or enzymes and sugars contained in the collected product may be reused.

The collected product obtained in Step (c) is preferably further subjected to solid-liquid separation in Step (d) to collect sugars contained in the collected product to reduce loss of the sugars. The method of the solid-liquid separation is not limited, and the solid-liquid separation may be carried out using a centrifuge and/or the like. Centrifugation of the collected liquid using a centrifuge produces a centrifugation supernatant having a lower turbidity compared to a case where solid-liquid separation of the saccharified liquid itself is carried out using a centrifuge. Thus, a clearer solution can be obtained.

As the centrifuge, for example, a disk-type (De Laval-type) centrifuge or a screw decanter-type centrifuge may be used.

The pH of the collected product may be adjusted before the centrifugation treatment. The pH is not limited, and is preferably not less than 6 from the viewpoint of reduction of the turbidity of the centrifugation supernatant. Ammonia, sodium hydroxide, potassium hydroxide, calcium hydroxide, or the like may be used for the pH-adjusting solution. Although the pH-adjusting solution may be added immediately before the centrifugation treatment, it is preferably used as the backwashing liquid for adjusting the pH of the collected product, from the viewpoint of increasing the washing effect by the backwashing.

The liquid fraction obtained by the treatment using a centrifuge may be subjected to Step (a), and mixed with the saccharified liquid before the microfiltration membrane treatment. By this, an increase in the solid component concentration in the enzymatically saccharified liquid can be alleviated while reducing loss of sugars.

EXAMPLES

Examples of our methods are described below.

Reference Example 1: Measurement of Lignin Content and Glucan Content

The lignin content in a pretreated product of cellulose-containing biomass was measured by referring to A. Sluiter and seven other authors, "Determination of Structural Carbohydrates and Lignin in Biomass," National Renewable Energy Laboratory (NREL), April 2008, Revision August 2012. In a beaker, 0.3 g of a pretreated product of cellulose-containing biomass was placed, and 3 mL of 72% sulfuric acid was added thereto, followed by leaving the resulting mixture to stand at 30° C. for 1 hour while occasionally stirring the mixture. While the resulting reaction liquid was mixed with 84 mL of purified water, the liquid was completely transferred into a pressure bottle, followed by autoclaving at 120° C. for 1 hour. After the hydrolysis, the resulting product was separated into the residue and the lysate by filtration. The filtrate and a water-washed liquid of the residue were combined to prepare 100 mL of a hydrolysate. The residue was dried at 105° C., and its weight was measured. The ash content in the residue was determined by heating with strong heat at 600° C. The amount of acid-insoluble lignin determined by subtracting the amount of the ash component in the hydrolysis residue from the amount of the residue was provided as the amount of lignin contained in the pretreated product of biomass. Based on the amount of lignin contained, the lignin content was calculated according to Equation (1).

Glucose and xylose in the hydrolysate were analyzed by HPLC under the following conditions, and quantified by comparison with standard samples. From the amount of glucose determined, the glucan content (%) was calculated according to the Equation (2).

HPLC Conditions
Column: Asahipak NH2P-50 4E (manufactured by Shodex)
Mobile phase: 0.5% phosphoric acid ultrapure water/0.5% phosphoric acid acetonitrile=12/88 (vol.) (flow rate, 1.0 ml/min.)
Reaction liquid: phosphoric acid/acetic acid/phenylhydrazine=220/180/6 (vol.) (flow rate, 0.4 ml/min.)
Detection method: fluorescence detection
Column oven temperature: 40° C.
Reaction vessel temperature: 150° C.

Reference Example 2: Method of Measuring MLSS Concentration

As an index of the amount of the solid component in the saccharified liquid, MLSS (Mixed Liquor Suspended Solids) was used. Measurement of MLSS was carried out according to JIS K 0102 14.1 (2008), which is based on the Japanese Industrial Standard. Glass fiber filter paper (manufactured by ADVANTEC Toyo Roshi Kaisha, Ltd.; GS-25) was placed on a filtration filter holder (manufactured by ADVANTEC Toyo Roshi Kaisha, Ltd.; KP-47S), and suction filtration of about 200 mL of RO water was carried out, followed by heating at 105° C. for 1 hour and measurement of the weight (a mg) of the glass fiber filter paper. Subsequently, suction filtration of V mL of a sample liquid was carried out using the dried glass fiber filter paper. The glass fiber filter paper was heated again at 105° C. for 2 hours, and then its weight (b mg) was measured, followed by calculating the MLSS concentration according to Equation (6). For obtaining better reproducibility in the measurement, the value V was controlled such that the value b falls within the range of 20 to 40 mg.

$$\text{MLSS concentration (mg/L)} = (b-a) \text{ (mg)}/V \text{ (mL)} \times 1000 \quad (6)$$

Reference Example 3: Preparation of Saccharified Liquid of Pretreated Product of Cellulose-Containing Biomass After measuring the moisture content of the pretreated product of cellulose-containing biomass, RO water was added such that the solid component concentration became 5% by weight in terms of the absolute-drying-processed biomass. The pH was adjusted to 5. After addition of Accellerase DUET (manufactured by Danisco Japan), hydrolysis reaction was allowed to proceed at 50° C. for 24 hours with stirring, to obtain a saccharified liquid of the pretreated product of cellulose-containing biomass.

Reference Example 4: Measurement of Turbidity

The turbidity was measured using a high-performance laboratory turbidimeter (2100N) manufactured by HACH.

Reference Example 5: Measurement of Sugar Concentration

The amounts of glucose and xylose were analyzed by HPLC under the following conditions, and quantified by comparison with standard samples.
Column: Luna NH2 (manufactured by Phenomenex, Inc.)
Mobile phase: Ultrapure water:acetonitrile=25:75 (flow rate, 0.6 mL/min.)
Reaction liquid: none
Detection method: RI (differential refractive index)
Temperature: 30° C.

Reference Example 6: Measurement of Cellobiose-Degrading Activity

In 50 mM sodium acetate buffer (pH 5.2), D(+)-cellobiose (manufactured by Wako Pure Chemical Industries, Ltd.) was dissolved at 15 mM to provide a substrate solution. To 500 μL of the substrate solution, 5 μL of the enzyme was added, and the reaction was allowed to proceed for 0.5 hour while the mixture was mixed by rotation at 50° C. Thereafter, the tube was centrifuged, and the glucose concentration in the supernatant component was measured by the method in Reference Example 5. The concentration of the produced glucose (g/L) was used as it is as the activity value of the cellobiose-degrading activity.

Reference Example 7: Solid-Liquid Separation of Hydrothermally Treated Bagasse Saccharified Liquid by Filter Press Bagasse (Taito-nosan) was immersed in water, and subjected to autoclaving (manufactured by Nitto Koatsu Co., Ltd.) with stirring at a temperature of 200° C. for 20 minutes. The pressure during the autoclaving was 7 MPa. Thereafter, solid-liquid separation into the solution component and the solid component was carried out. The lignin content in the resulting solid component as a hydrothermally treated bagasse was calculated by the method in Reference Example 1. As a result, the lignin content was 12%. A saccharified liquid was obtained by the method in Reference Example 3. In this process, the pH was adjusted to 5 using an aqueous sodium hydroxide solution.

Solid-liquid separation by filter press was attempted using 2 L of the saccharified liquid obtained. For the filter press, a compact filtration device MO-4 manufactured by Yabuta Industries Co., Ltd. was used. As a result of treatment at 0.05 MPa for 5 minutes, 1200 mL of filtrate could be obtained. It could be confirmed that solid-liquid separation by filter press, which is a conventional method, is effective for a saccharified liquid of a pretreated product of cellulose-containing biomass having a lignin content of 12%.

Comparative Example 1: Solid-Liquid Separation of Unbleached Hardwood Kraft Pulp Saccharified Liquid by Filter Press As an unbleached hardwood kraft pulp, sheet wet pulp (manufactured by Hyogo Pulp Co., Ltd.) was used. The lignin content and the glucan content in the sheet wet pulp were measured by the method in Reference Example 1.

The lignin content in the sheet wet pulp was 1%. The glucan content was 73%.

From the sheet wet pulp, a saccharified liquid was obtained by the method in Reference Example 3. By addition of sodium acetate buffer (pH 5.2) at 100 mM, the pH was adjusted to 5. Solid-liquid separation by filter press was attempted using 2 L of the saccharified liquid obtained. For the filter press, a compact filtration device MO-4 manufactured by Yabuta Industries Co., Ltd. was used. As a result of treatment at 0.05 MPa for 5 minutes, only 80 mL of filtrate could be obtained. The filtration rate decreased to about 1/10 compared to that in Reference Example 7. Solid-liquid separation by a filter press method is insufficient for a saccharified liquid of a pretreated product of cellulose-containing biomass having a low lignin content, and the method cannot be said to be a cost-effective solid-liquid separation method.

Comparative Example 2

The same unbleached hardwood kraft pulp saccharified liquid as in Comparative Example 1 was placed in a centrifuge, and centrifugation was carried out at 1500 G for 1 minute, followed by collecting the resulting supernatant. The turbidity of the centrifugation supernatant was measured by the method in Reference Example 4. The result is shown in Table 1. The centrifugation supernatant showed a turbidity of as high as 680 NTU. Thus, centrifugation, which is a conventional method, failed to achieve sufficient solid-liquid separation of a saccharified liquid of a pretreated product of cellulose-containing biomass having a lignin content of 1%.

TABLE 1

|  | Lignin content of pretreated product of biomass (%) | Turbidity (NTU) |
| --- | --- | --- |
| Comparative Example 2 | 1 | 680 |
| Example 1 | 1 | 0 |
| Example 2 | 4 | 0.9 |
| Example 3 | 6 | 1 |
| Example 4 | 8.5 | 1 |

Example 1: Total Circulation Filtration Operation for Unbleached Hardwood Kraft Pulp Saccharified Liquid To a microfiltration membrane, 2 L of the same saccharified liquid as in Comparative Example 1 was supplied at a temperature of 30° C. at a membrane surface linear velocity of 30 cm/sec. using a tube pump. While performing cross-flow filtration at a filtration rate of 0.5 m/d, the filtrate was returned to the supply tank, to perform total circulation operation. In terms of the microfiltration membrane, a hollow fiber membrane made of polyvinylidene fluoride having a nominal pore size of 0.05 μm used in a microfiltration membrane module manufactured by Toray Industries, Inc. "TORAYFIL (registered trademark)" HFS was cut out to prepare a miniature module composed of 22 hollow fiber membranes having an internal diameter of 10 mm and a length of 320 mm. Cross-flow filtration was carried out for 28 minutes, and backwashing was carried out using RO water for 2 minutes at 1.5 m/day. The collected product was collected to the outside of the filtration system. While the cycle from the filtration to the backwashing was repeated, air washing was carried out after every 10 cycles to collect cakes on the membrane surface that could not be collected by the backwashing. In the air washing, an operation of blowing air into the feed side of the module at 0.8 L/min. for 10 seconds to peel off the cake formed on the membrane surface, and subsequently sending RO water to the feed side of the module at 30 cm/sec. for 30 seconds to collect the peeled cake, was repeated eight times. The MLSS concentration in supply tank was measured by the method in Reference Example 2. The ratio of the MLSS concentration after every 10 cycles to the MLSS concentration before the filtration was defined as the solid component ratio (%), and calculated according to Equation (7):

Solid component ratio (%)=MLSS concentration after every 10 cycles/MLSS concentration before the filtration×100     (7).

The results of calculation of the solid component ratios after the 10th cycle and after the 20th cycle are shown in Table 2. From these results, it was found that, as the number of cycles increases, the solid component ratio decreases. The solid-liquid separation with the microfiltration membrane was effective for the unbleached hardwood pulp saccharified liquid having a lignin content of 1%. By calculating the transmembrane pressure difference, the degree of clogging of the membrane was evaluated. The transmembrane pressure difference was calculated according to Equation (4) by measurement of the module-inlet pressure (P1), module-outlet pressure (P2), and permeate-side pressure (P3). The transmembrane pressure difference in the beginning of the filtration was subtracted from the transmembrane pressure difference at the time of the measurement to calculate the pressure difference increase. The value upon completion of the filtration at the 20th cycle is shown in Table 2. The pressure difference increase was 2 kPa. Thus, an increase in the pressure difference due to clogging of the membrane could be suppressed by the collection of the solid component on the membrane surface.

Turbidity of the obtained sugar liquid was measured by the method in Reference Example 4. The result is shown in Table 1. The turbidity was remarkably decreased relative to the case of Comparative Example 2. Thus, effectiveness of the solid-liquid separation by microfiltration was demonstrated also by this result.

Example 2: Total Circulation Filtration Operation for Unbleached Softwood Kraft Pulp Saccharified Liquid As an unbleached softwood kraft pulp, Cellofiber (manufactured by Hyogo Pulp Co., Ltd.) was used. The lignin content in Cellofiber was measured by the method in Reference Example 1. As a result, the lignin content was found to be 4%. The glucan content was 77%. A saccharified liquid was obtained from the Cellofiber by the method in Reference Example 3. By addition of sodium acetate buffer (pH 5.2) at 100 mM, the pH was adjusted to 5.

Total circulation filtration was carried out for 2 L of the saccharified liquid under the same filtration conditions using the same microfiltration membrane as in Example 1. The solid component ratio after every 10 cycles and the pressure difference increase at the 20th cycle are shown in Table 2. The unbleached softwood pulp saccharified liquid having a lignin content of 4% tended to show a decrease in the solid component ratio (%) similarly to Example 1. Thus, the solid-liquid separation with the microfiltration membrane was effective. The pressure difference increase was 2 kPa. Thus, an increase in the pressure difference due to clogging of the membrane could be suppressed by the collection of the cake formed on the membrane surface, similarly to Example 1.

The turbidity of the obtained sugar liquid was measured by the method in Reference Example 4. The result is shown in Table 1. The turbidity was remarkably decreased relative to the case of Comparative Example 2. Thus, effectiveness of the solid-liquid separation by microfiltration was demonstrated also by this result.

Example 3: Total Circulation Filtration of Acetic-Acid-Treated Corncob Saccharified Liquid Normal-pressure acetic acid pulping was carried out referring to JP 3811833 B. To corncob (Nippon Walnut Co., Ltd.), 80% acetic acid water and 72% sulfuric acid were added to achieve a concentration of 0.32%, and the resulting mixture was boiled for 4 hours, followed by stopping the heating. The solid component was separated by suction filtration, and then sufficiently washed with water, to obtain an acetic-acid-treated corncob. The lignin content in the acetic-acid-treated corncob was measured by the method in Reference Example 1. As a result, the lignin content was found to be 6%. The glucan content was 71%. A saccharified liquid was obtained by the method in Reference Example 3. In this process, the pH was adjusted to 5 using an aqueous sodium hydroxide solution.

Total circulation filtration was carried out for 2 L of the saccharified liquid under the same filtration conditions using the same microfiltration membrane as in Example 1. The solid component ratio after every 10 cycles and the pressure difference increase at the 20th cycle are shown in Table 2. The acetic-acid-treated corncob saccharified liquid having a lignin content of 6% tended to show a decrease in the solid component ratio (%) similarly to Examples 1 and 2. Thus, separation of the solid component by the filtration through the microfiltration membrane was effective. The pressure difference increase was 4 kPa. Thus, an increase in the transmembrane pressure difference due to clogging of the membrane could be suppressed by the collection of the cake formed on the membrane surface, similarly to Examples 1 and 2.

The turbidity of the obtained sugar liquid was measured by the method in Reference Example 4. The result is shown in Table 1. The turbidity was remarkably decreased relative to the case of Comparative Example 2. Thus, effectiveness of the solid-liquid separation with the microfiltration membrane was demonstrated.

Example 4: Total Circulation Filtration of Acetic-Acid-Treated Sawdust Saccharified Liquid Normal-pressure acetic acid pulping was carried out referring to JP 3811833 B. To sawdust, 80% acetic acid water and 72% sulfuric acid were added to achieve a concentration of 0.32%, and the resulting mixture was boiled for 4 hours, followed by stopping the heating. The solid component was separated by suction filtration, and then sufficiently washed with water, to obtain an acetic-acid-treated corncob. The lignin content in the acetic-acid-treated corncob was measured by the method in Reference Example 1. As a result, the lignin content was found to be 8.5%. The glucan content was 75%. A saccharified liquid was obtained by the method in Reference Example 3. In this process, the pH was adjusted to 5 using an aqueous sodium hydroxide solution.

Total circulation filtration was carried out for 2 L of the saccharified liquid under the same filtration conditions using the same microfiltration membrane as in Example 1. The solid component ratio after every 10 cycles and the pressure difference increase at the 20th cycle are shown in Table 2. The acetic-acid-treated sawdust saccharified liquid having a lignin content of 8.5% tended to show a decrease in the solid component ratio (%) similarly to Examples 1 and 2. Thus, separation of the solid component by the filtration through the microfiltration membrane was effective. The pressure difference increase was 6 kPa. Thus, an increase in the transmembrane pressure difference due to clogging of the membrane could be suppressed by the collection of the cake formed on the membrane surface, similarly to Examples 1, 2, and 3.

The turbidity of the obtained sugar liquid was measured by the method in Reference Example 4. The result is shown in Table 1. The turbidity was remarkably decreased relative to the case of Comparative Example 2. Thus, effectiveness of the solid-liquid separation with the microfiltration membrane was demonstrated.

Comparative Example 3: Total Circulation Filtration of Saccharified Liquid of Ammonia-Treated Bagasse Bagasse (Taito-nosan) was fed to a compact reactor (manufactured by Taiatsu Techno Corporation, TVS-N2 30 mL), and cooled with liquid nitrogen. To this reactor, ammonia gas was fed to immerse the sample completely in liquid ammonia. After closing the lid of the reactor, the reactor was left to stand at room temperature for about 15 minutes. Subsequently, treatment in an oil bath at 150° C. was carried out for 1 hour. Thereafter, the reactor was removed from the oil bath, and the ammonia gas was immediately leaked in a fume hood, followed by vacuuming the inside of the reactor to 10 Pa with a vacuum pump, thereby drying the content. The lignin content in the ammonia-treated bagasse was measured by the method in Reference Example 1. As a result, the lignin content was found to be 18%. A saccharified liquid was obtained by the method in Reference Example 3. In this process, the pH was adjusted to 5 using sulfuric acid.

Total circulation filtration was carried out for 2 L of the saccharified liquid under the same filtration conditions using the same microfiltration membrane as in Example 1. The solid component ratio after every 10 cycles and the pressure difference increase at the 20th cycle are shown in Table 2. As shown by these results, the solid component ratio (%) remained at almost the same level through the cycles, and formation of a thick cake layer did not occur with the ammonia-treated bagasse saccharified liquid having a lignin content of 18%. Sufficient separation of the solid component by the filtration through the microfiltration membrane was therefore impossible. The pressure difference increase was 70 kPa, and the transmembrane pressure difference was higher than those in Examples 1 to 4. Thus, the filtration performance was low.

Comparative Example 4: Total Circulation Filtration of Saccharified Liquid of Hydrothermally Treated Bagasse Bagasse (Taito-nosan) was immersed in water, and subjected to autoclaving (manufactured by Nitto Koatsu Co., Ltd.) with stirring at a temperature of 200° C. for 20 minutes. The pressure during the autoclaving was 7 MPa. Thereafter, solid-liquid separation into the solution component and the solid component was carried out. The lignin content in the resulting solid component as a hydrothermally treated bagasse was calculated by the method in Reference Example 1. As a result, the lignin content was found to be 12%. A saccharified liquid was obtained by the method in Reference Example 3. In this process, the pH was adjusted to 5 using an aqueous sodium hydroxide solution.

Total circulation filtration was carried out for 2 L of the saccharified liquid under the same filtration conditions using the same microfiltration membrane as in Example 1. The solid component ratio after every 10 cycles and the pressure difference increase at the 20th cycle are shown in Table 2. According to these results, the solid component ratio (%) remained at almost the same level through the cycles, and formation of a thick cake layer on the membrane surface did not occur with the hydrothermally treated bagasse saccharified liquid having a lignin content of 12%. Sufficient separation of the solid component by the filtration through the microfiltration membrane was therefore impossible. The pressure difference increase was 50 kPa, and the transmembrane pressure difference was higher than those in Examples 1 to 4. Thus, the filtration performance was low.

Comparative Example 5: Total Circulation Filtration of NaOH-Treated Corncob Saccharified Liquid To corncob (Nippon Walnut Co., Ltd.), sodium hydroxide was added such that the amount of the sodium hydroxide was 30 mg per 1 g of the corncob. The resulting mixture was allowed to react at room temperature for 24 hours with stirring, and then solid-liquid separation was carried out. The lignin content was calculated by the method in Reference Example 1. As a result, the lignin content was found to be 10%. A saccharified liquid was obtained by the method in Reference Example 3. In this process, the pH was adjusted to 5 using sulfuric acid. Total circulation filtration was carried out for 2 L of the saccharified liquid under the same filtration conditions using the same microfiltration membrane as in Example 1. The solid component ratio after every 10 cycles and the pressure difference increase at the 20th cycle are shown in Table 2. According to these results, the solid component ratio (%) remained at almost the same level through the cycles, and formation of a thick cake layer did not occur with the NaOH-treated corncob saccharified liquid having a lignin content of 10%. Sufficient separation of the solid component by the filtration through the microfiltration membrane was therefore impossible. The pressure difference increase was 50 kPa, and the transmembrane pressure difference was higher than those in Examples 1 to 4. Thus, the filtration performance was low.

TABLE 2

|  | Lignin content of pretreated product of biomass (%) | Pressure difference increase at 20th cycle (kPa) | Solid component ratio at 10th cycle (%) | Solid component ratio at 20th cycle (%) |
| --- | --- | --- | --- | --- |
| Example 1 | 1 | 2 | 84 | 74 |
| Example 2 | 4 | 2 | 82 | 70 |
| Example 3 | 6 | 4 | 80 | 69 |
| Example 4 | 8.5 | 6 | 85 | 76 |
| Comparative Example 3 | 18 | 70 | 98 | 98 |
| Comparative Example 4 | 12 | 50 | 96 | 95 |
| Comparative Example 5 | 10 | 50 | 95 | 93 |

Example 5: Filtration of Hardwood Pulp Saccharified Liquid

The same unbleached hardwood kraft pulp saccharified liquid and the same microfiltration membrane as in Example 1 were used. To the saccharified liquid supply tank, 700 mL of the saccharified liquid was placed, and cross-flow filtration was carried out at 30° C., a membrane surface linear velocity of 30 cm/sec., and a permeation flow rate of 0.5 m/day. While performing the filtration, the saccharified liquid in the same volume as the filtration volume was continuously supplied to the saccharified liquid supply tank to keep the liquid volume in the saccharified liquid supply tank constant.

By calculating the transmembrane pressure difference, the degree of clogging of the membrane was evaluated. The transmembrane pressure difference was calculated according to Equation (4) by measurement of the module-inlet pressure (P1), module-outlet pressure (P2), and permeate-side pressure (P3). The transmembrane pressure difference in the beginning of the filtration was subtracted from the transmembrane pressure difference at the time of the measurement to calculate the pressure difference increase. The transmembrane pressure difference was measured every 28 minutes to calculate the pressure difference increase. The results are shown in FIG. 1 and Table 3. As a result, the pressure difference increase exceeded 50 kPa when the filtration was carried out for 112 minutes. The filtration was stopped at this time point, and the cake formed on the membrane surface was peeled off and collected.

Example 6: Effect of Backwashing

The same unbleached hardwood kraft pulp saccharified liquid and the same microfiltration membrane as in Example 1 were used. To the saccharified liquid supply tank, 700 mL of the saccharified liquid was placed, and cross-flow filtration was carried out at 30° C., a membrane surface linear velocity of 30 cm/sec., and a permeation flow rate of 0.5 m/day. While performing the filtration, the saccharified liquid in the same volume as the filtration volume was continuously supplied to the saccharified liquid supply tank to keep the liquid volume in the saccharified liquid supply tank constant.

Filtration was carried out for 28 minutes, and backwashing was carried out by supplying RO water from the permeate side to the feed side for 2 minutes at 1.5 m/day. The cake formed on the membrane surface was collected to the outside of the filtration system. Twenty-eight minutes of cross-flow filtration and 2 minutes of backwashing were alternately carried out. A cycle of the filtration and the backwashing, in this order, was repeated 11 times. The pressure difference increase was calculated in the same manner as in Example 5. The results are shown in FIG. 1. The pressure difference increases upon completion of the filtration in the 4th cycle and the 11th cycle are shown in Table 3. The pressure difference increase at the 11th cycle was 23 kPa. As shown by these results, by periodically carrying out backwashing to peel off and collect the cake from the membrane surface, an increase in the transmembrane pressure difference could be suppressed, and the operation could be carried out for a long time without decreasing the filtration performance.

Example 7: Effect of Removal of Liquid in Module and Backwashing

The same unbleached hardwood kraft pulp saccharified liquid as in Example 1 was used as the saccharified liquid. Cross-flow filtration was carried out for 28 minutes under the same conditions as in Example 6, and the saccharified liquid remaining in the feed side in the module after the stopping of the filtration was removed from the bottom part of the module to empty the module. Thereafter, in the state where the inside of the module is empty, RO water was supplied from the permeate side to the feed side for 2 minutes at 1.5 m/day to perform backwashing similarly to Example 6, and the cake formed on the membrane surface was collected to the outside of the filtration system by removal from the bottom part of the module.

A cycle of the cross-flow filtration, removal of the saccharified liquid in the module, and backwashing was repeated 11 times. The pressure difference increase was calculated in the same manner as in Example 5. The results are shown in FIG. 1. The pressure difference increases upon completion of the filtration in the 4th cycle and the 11th cycle are shown in Table 3. The pressure difference increase observed upon the completion of the 11th cycle was 4 kPa. The transmembrane pressure difference in the beginning of the filtration was 3 kPa.

As shown by the pressure difference increase observed upon the completion of the 11th cycle, by carrying out backwashing in a state where the inside of the module is empty, an increase in the transmembrane pressure difference could be suppressed better than in the case where only backwashing with RO water was carried out in Example 6, and the operation could be carried out for a long time without decreasing the filtration performance.

TABLE 3

|  | Transmembrane pressure difference in beginning of filtration (kPa) | Pressure difference increase at 4th cycle (kPa) | Pressure difference increase at 11th cycle (kPa) |
| --- | --- | --- | --- |
| Example 5 | 3 | 59 | — |
| Example 6 | 2 | 3.5 | 23 |
| Example 7 | 3 | 2 | 4 |
| Example 9 | 2 | 4 | 25 |
| Example 10 | 2 | 7 | 32 |
| Example 11 | 2 | 8 | 42 |

Example 8: Effect of Combination of Removal of Liquid in Module, Backwashing, and Air Washing For the microfiltration membrane showing an increased transmembrane pressure difference after the 11 cycles in the operation method in Example 6, air-washing operation was carried out. In the air washing, an operation of blowing air into the feed side of the module at 0.8 L/min. for 10 seconds to peel off the cake, and sending RO water to the feed side of the module at 30 cm/sec. for 30 seconds to flush out and collect the peeled cake, was repeated eight times. By carrying out the air washing, a cake that could not be peeled off from the membrane surface by simply carrying out the backwashing could be peed off and collected. When filtration was carried out under the same filtration conditions as in Example 6 after carrying out the air washing, the pressure difference increase in the beginning of the filtration was found to be 0 kPa. We found that, by carrying out air washing at the time when the transmembrane pressure difference increases, the effect to peel off the cake formed on the membrane surface can be increased. By combination of the air washing with the discharging from the module and the backwashing, the operation can be carried out for a longer time without decreasing the filtration performance.

Example 9: Filtration of Unbleached Softwood Kraft Pulp Saccharified Liquid

The same unbleached softwood kraft pulp saccharified liquid and the same microfiltration membrane as in Example 2 were used. Filtration and backwashing were carried out by the same method as in Example 6. A cycle of the filtration and the backwashing, in this order, was repeated 11 times. The pressure difference increase was calculated in the same manner as in Example 5. The results are shown in FIG. 1. The pressure difference increases upon completion of the 4th cycle and the 11th cycle are shown in Table 3. The pressure difference increase at the 11th cycle was 25 kPa.

Example 10: Filtration of Acetic-Acid-Treated Corncob Saccharified Liquid

The same acetic-acid-treated corncob saccharified liquid and the same microfiltration membrane as in Example 3 were used. Filtration and backwashing were carried out by the same method as in Example 6. A cycle of the filtration and the backwashing, in this order, was repeated 11 times. The pressure difference increase was calculated in the same manner as in Example 5. The results are shown in FIG. 1. The pressure difference increases upon completion of the 4th cycle and the 11th cycle are shown in Table 3. The pressure difference increase at the 11th cycle was 32 kPa.

Example 11: Filtration of Acetic-Acid-Treated Sawdust Saccharified Liquid

The same acetic-acid-treated sawdust saccharified liquid and the same microfiltration membrane as in Example 4 were used. Filtration and backwashing were carried out by the same method as in Example 6. A cycle of the filtration and the backwashing, in this order, was repeated 11 times. The pressure difference increase was calculated in the same manner as in Example 5. The results are shown in FIG. 1. The pressure difference increases upon completion of the 4th cycle and the 11th cycle are shown in Table 3. The pressure difference increase at the 11th cycle was 42 kPa.

Example 12: Centrifugation of Collected Product

The collected product (pH 5) peeled off from the membrane by backwashing in Example 6 was centrifuged at 1500 G for 1 minute using a centrifuge, and the resulting supernatant was collected. The turbidity of the centrifugation supernatant was measured by the method in Reference Example 4. The results are shown in Table 4.

The sugar concentration in the collected supernatant, the sugar concentration in the saccharified liquid used in Example 6, and the sugar concentration in the permeate in Example 6 were measured, and the amount of sugar (%) in the total collected product and the amount of sugar (%) in the total permeate (%) with respect to the total amount of sugar fed in Example 6 were calculated for each of glucose and xylose using Equation (8):

Amount of sugar (%)=amount of sugar in the total collected product or total permeate (g)/total amount of sugar fed (g)×100 (8).

As a result, we found that, in the process of obtaining the total permeate containing glucose and xylose in an amount corresponding to 63% of the total amount of sugar fed, glucose and xylose in an amount corresponding to 4% of the total amount of sugar fed could be collected by the centrifugation. By mixing the centrifugation supernatant with the enzymatically saccharified liquid before the microfiltration membrane treatment, sugar could be collected also from the collected product.

Through an ultrafiltration membrane having a molecular weight cutoff of 10,000 (VIVASPIN 20, manufactured by Saritorius stedim biotech; material: PES), 15 mL of the above supernatant was filtered. Centrifugation was carried out at 8000 G until the feed side decreased to not more than 1 mL. The non-permeate was diluted 10-fold with RO water, and centrifuged again at 8000 G to collect the non-permeate. The cellobiose-degrading activity of the obtained non-permeate was measured by the method in Reference Example 6.

TABLE 4

|  | pH | Turbidity of centrifugation supernatant (NTU) |
|---|---|---|
| Example 12 | 5 | 460 |
| Example 13 | 6 | 360 |
|  | 7 | 340 |
|  | 8 | 120 |
|  | 9 | 100 |

Example 13: Centrifugation of Collected Product Whose pH was Adjusted to 6, 7, 8, or 9

The pH of the collected product collected to the outside of the filtration system by the backwashing in Example 6 was adjusted to 6, 7, 8, or 9 with an aqueous sodium hydroxide solution, and centrifugation was carried out in the same manner as in Example 12. The turbidity of each centrifugation supernatant was measured by the method in Reference Example 4. The results are shown in Table 4. In any case, a supernatant having a turbidity lower than that in the case of pH 5 could be obtained. We thus found that the solid-liquid separation performance can be increased by adjusting the pH of the collected product to not less than 6.

Further, in the same manner as in Example 12, each supernatant obtained by the adjustment of the pH to 6, 7, 8, or 9 followed by the centrifugation was filtered through an ultrafiltration membrane to obtain a non-permeate. The cellobiose-degrading activity of the obtained non-permeate was measured by the method in Reference Example 6. The ratio of the activity value under the conditions of pH 6, 7, 8, or 9 to the activity value under the conditions of pH 5 in Example 12, which is taken as 1, was determined to calculate the relative cellobiose-degrading activity. The results are shown in Table 5. We found that the cellobiose-degrading activity under conditions where the pH is not less than 6 is higher than that under conditions where the pH is 5.

TABLE 5

|  | pH | Relative cellobiose-degrading activity |
|---|---|---|
| Example 12 | 5 | 1 |
| Example 13 | 6 | 2.5 |
|  | 7 | 3.1 |
|  | 8 | 3.7 |
|  | 9 | 3.7 |

Example 14: Operation Using Backwashing Liquid at pH 5, 6, 9, or 11

Under the same operation conditions as in Example 6, filtration and backwashing of an unbleached hardwood kraft pulp saccharified liquid were carried out. The backwashing liquid was prepared by adjusting the pH of RO water to 5, 6, 9, or 11 using sulfuric acid and sodium hydroxide. A cycle of performing filtration followed by backwashing was repeated five times. The pressure difference increase upon completion of the filtration in each cycle is shown in Table 6. The pressure difference increase was calculated in the same manner as in Example 4. The transmembrane pressure difference in the beginning of the filtration in the operation using each backwashing liquid was 2 kPa in all cases. The values obtained by the backwashing using the backwashing liquid at a pH of 5, 6, 9, or 11 are shown in Table 6. We found that an increase in the transmembrane pressure difference can be suppressed by carrying out backwashing using a backwashing liquid whose pH is adjusted to a higher value.

TABLE 6

| | | Pressure difference increase (kPa) | | | | |
|---|---|---|---|---|---|---|
| | pH | Cycle 1 | Cycle 2 | Cycle 3 | Cycle 4 | Cycle 5 |
| Example 14 | 5 | 2 | 3.5 | 4.5 | 6 | 7.5 |
| | 6 | 2 | 2.5 | 3 | 3 | 4 |
| | 9 | 2 | 2.5 | 2.5 | 2.5 | 3 |
| | 11 | 2 | 2.5 | 2.5 | 2.5 | 2.5 |

Example 15: Decreases in Membrane Surface Linear Velocity and Solid Component Ratio Using the same unbleached hardwood kraft pulp saccharified liquid as in Example 1, the same total circulation operation as in Example 1 was carried out at a membrane surface linear velocity of 10 cm/sec. or 50 cm/sec. The solid component ratio (%) in the saccharified liquid in the feed side at the 10th cycle was calculated. The results are shown in Table 7. Under the conditions where the membrane surface linear velocity was 10 cm/sec., the solid component ratio was 80%. Under the conditions where the membrane surface linear velocity was 30 cm/sec., the solid component ratio was 84%. Under the conditions where the membrane surface linear velocity was 50 cm/sec., the solid component ratio was 89%.

TABLE 7

| | Membrane surface linear velocity | Solid component ratio (%) |
|---|---|---|
| Example 1 | 30 cm/sec | 84 |
| Example 15 | 10 cm/sec | 80 |
| | 50 cm/sec | 89 |

INDUSTRIAL APPLICABILITY

Our methods can be utilized in industries in which sugar liquids are produced from cellulose-containing biomass.

The invention claimed is:

1. A method of producing a sugar liquid derived from a cellulose-containing biomass comprising:
   (a) enzymatically saccharifying a pretreated product having a lignin content of 1% to 8.5% obtained by pretreatment of a cellulose-containing biomass, to obtain a saccharified liquid;
   (b) filtering the saccharified liquid obtained in Step (a) through a microfiltration membrane to promote formation of a cake layer on a membrane surface in a feed side while obtaining a sugar liquid from a permeate side; and
   (c) collecting the cake layer formed on the membrane surface in Step (b) by peeling from the membrane;
   wherein the Step (b), the saccharified liquid obtained in Step (a) is directly filtered through the microfiltration membrane.

2. The method according to claim 1, wherein said pretreated product of a cellulose-containing biomass is a chemical pulp.

3. The method according to claim 2, wherein the lignin content in said pretreated product of a cellulose-containing biomass is 1% to 6%.

4. The method according to claim 2, wherein the filtration in Step (b) is cross-flow filtration.

5. The method according to claim 2, wherein peeling the cake in Step (c) is performed by backwashing and/or air washing the membrane surface.

6. The method according to claim 1, wherein the lignin content in said pretreated product of a cellulose-containing biomass is 1% to 6%.

7. The method according to claim 6, wherein the filtration in Step (b) is cross-flow filtration.

8. The method according to claim 6, wherein peeling the cake in Step (c) is performed by backwashing and/or air washing the membrane surface.

9. The method according to claim 1, wherein the filtration in Step (b) is cross-flow filtration.

10. The method according to claim 9, wherein a membrane surface linear velocity in said cross-flow filtration is 10 cm/sec. to 30 cm/sec.

11. The method according to claim 9, wherein peeling the cake in Step (c) is performed by backwashing and/or air washing the membrane surface.

12. The method according to claim 10, wherein peeling the cake in Step (c) is performed by backwashing and/or air washing the membrane surface.

13. The method according to claim 1, wherein peeling the cake in Step (c) is performed by backwashing and/or air washing the membrane surface.

14. The method according to claim 13, wherein an aqueous solution at a pH of not less than 6 is used for said backwashing.

15. A method of producing a sugar liquid derived from a cellulose-containing biomass comprising:
   (a) saccharifying a pretreated product having a lignin content of 1% to 8.5% obtained by pretreatment of a cellulose-containing biomass, to obtain a saccharified liquid;
   (b) filtering the saccharified liquid obtained in Step (a) through a microfiltration membrane to promote formation of a cake layer on a membrane surface in a feed side while obtaining a sugar liquid from a permeate side; and
   (c) collecting the cake layer formed on the membrane surface in Step (b) by peeling from the membrane;

wherein the Step (b), the saccharified liquid obtained in Step (a) is directly filtered through the microfiltration membrane by constant flow filtration.

\* \* \* \* \*